United States Patent
Jerebko (10) Patent No.: US 9,192,340 B2
(45) Date of Patent: Nov. 24, 2015

(54) IMAGING METHOD AND APPARATUS WITH OPTIMIZED GRAYSCALE VALUE WINDOW DETERMINATION

(75) Inventor: Anna Jerebko, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 729 days.

(21) Appl. No.: 13/358,002

(22) Filed: Jan. 25, 2012

(65) Prior Publication Data

US 2012/0189192 A1 Jul. 26, 2012

(30) Foreign Application Priority Data

Jan. 25, 2011 (DE) .......................... 10 2011 003 138

(51) Int. Cl.
| G06K 9/62 | (2006.01) |
| A61B 6/02 | (2006.01) |
| A61B 6/03 | (2006.01) |
| A61B 6/04 | (2006.01) |
| A61B 6/00 | (2006.01) |

(52) U.S. Cl.
CPC . *A61B 6/02* (2013.01); *A61B 6/466* (2013.01); *A61B 6/5217* (2013.01); *A61B 6/5229* (2013.01); *A61B 6/025* (2013.01); *A61B 6/03* (2013.01); *A61B 6/0421* (2013.01); *A61B 6/46* (2013.01); *A61B 6/502* (2013.01); *A61B 6/563* (2013.01)

(58) Field of Classification Search
None
See application file for complete search history.

(56) References Cited

U.S. PATENT DOCUMENTS

| 4,755,954 A | 7/1988 | Netter |
| 5,042,077 A | 8/1991 | Burke |
| 5,261,050 A | 11/1993 | Fox et al. |
| 5,305,204 A | 4/1994 | Ohhashi |
| 5,467,404 A | 11/1995 | Vuylsteke et al. |
| 5,900,732 A | 5/1999 | Felmlee et al. |
| 6,175,643 B1 | 1/2001 | Lai et al. |
| 7,218,763 B2 | 5/2007 | Belykh et al. |
| 7,945,014 B2 | 5/2011 | Mertelmeier |
| 7,965,812 B2 | 6/2011 | Hanke et al. |
| 2003/0179917 A1 | 9/2003 | Faber et al. |

(Continued)

FOREIGN PATENT DOCUMENTS

| DE | 10213284 A1 | 10/2003 |
| DE | 10324908 A1 | 12/2004 |

(Continued)

OTHER PUBLICATIONS

Arnulf Oppelt, "Imaging Systems for Medical Diagnostics", Book, 2005, pp. 47-48, John Wiley & Sons.

(Continued)

*Primary Examiner* — Kim Vu
*Assistant Examiner* — Fred Hu
(74) *Attorney, Agent, or Firm* — Laurence A. Greenberg; Werner H. Stemer; Ralph E. Locher (57) ABSTRACT

A self-learning imaging method is particularly suited radiation imaging, such as for mammography. A plurality of training data sets are displayed on a display apparatus. A grayscale value setting is selected for each training data set. A feature set with at least one feature is assigned to each training data set. The feature set and the grayscale value setting are stored for each training data set. The grayscale value setting of an examination data set is selected according to the feature sets and the grayscale value setting of the training data sets.

11 Claims, 6 Drawing Sheets

(56) References Cited

U.S. PATENT DOCUMENTS

| | | | | |
|---|---|---|---|---|
| 2004/0264756 | A1* | 12/2004 | Spahn | 382/132 |
| 2007/0052716 | A1* | 3/2007 | Jabri et al. | 345/581 |
| 2009/0310844 | A1 | 12/2009 | Ludwig et al. | |
| 2009/0323893 | A1 | 12/2009 | Hanke et al. | |
| 2010/0020920 | A1 | 1/2010 | Mertelmeier | |
| 2010/0034450 | A1 | 2/2010 | Mertelmeier | |
| 2011/0122992 | A1 | 5/2011 | Hanke et al. | |

FOREIGN PATENT DOCUMENTS

| | | |
|---|---|---|
| DE | 102006046741 A1 | 4/2008 |
| DE | 102008004473 A1 | 7/2009 |
| DE | 102008028387 A1 | 12/2009 |
| DE | 102008033150 A1 | 2/2010 |
| EP | 1840829 A2 * | 10/2007 |
| EP | 2138098 A1 | 12/2009 |

OTHER PUBLICATIONS

Evan J. Williams and Julian C. Stanley, Linear Hypotheses, International Encyclopedia of Statistics, 1978, I Regression, pp. 523-540, II Analysis of Variance, pp. 541-554, vol. 1, Free Press, New York, NY, USA.

David Birkes and Yadolah Dodge, "Alternative Methods of Regression", Wiley Series in Probability and Mathematical Statistics, Book, Jun. 1993, 240 Pages, Wiley-Interscience, New York, NY, USA.

Chris Chatfield, "Calculating Interval Forecasts", Journal of Business & Economic Statistics, Apr. 1993, pp. 121-135, vol. 11, No. 2, American Statistical Association, USA.

Gregory W. Corder and Dale I. Foreman, "Nonparametric Statistics for Non-Statisticians—A Step-By-Step Approach", Book, 2009, p. 247, John Wiley & Sons.

Norman R. Draper and Harry Smith, "Applied Regression Analysis", Book, Apr. 23, 1998, p. 736, Third Edition, Wiley-Interscience, New York, NY, USA.

John Fox, "Applied Regression Analysis, Linear Models and Related Methods", Book, Feb. 5, 1997, p. 624, Sage Publications, California, USA.

Wolfgang Haerdle, "Applied Nonparametric Regression", Econometric Society Monographs No. 19, Book, 1990, p. 333.

Nigel Meade and Towhdul Islam, "Prediction Intervals for Growth Curve Forecasts", Journal of Forecasting, 1995, pp. 413-430, vol. 14, John Wiley & Sons.

Noel Cressie, "Change of Support and the Modifiable Areal Unit Problem", Geographical Systems, 1996, pp. 159-180, vol. 3.

A. Stewart Fotheringham and Chris Brunsdon and Martin Charlton, "Geographically Weighted Regression the Analysis of Spatially Varying Relationships", Book, Oct. 18, 2002, pp. 282, John Wiley & Sons.

Roger Weber and Hans-J. Schek and Stephen Blott, "A Quantitative Analysis and Performance Study for Similarity-Search Methods in High-Dimensional Spaces", VLDB Proceedings of the 24th International Conference New York, pp. 194-205, 1998, Morgan Kaufmann, San Francisco, CA, USA.

Andrew W. Moore, "An Intoductory Tutorial on KD-Trees", Extract From Andrew Moore's PhD Thesis: Efficient Memory-Based Learning for Robot Control, Computer Laboratory Chapter 6, 1991, pp. 6-1-6-18, Technical Report No. 209.

D. T. Lee and C. K. Wong, "Worst-Case Analysis for Region and Partial Region Searches in Multidimensional Binary Search Trees and Balanced Quad Trees", Acta Information 9, Sep. 30, 1977, pp. 23-29.

Roger Weber and Stephen Blott, "An Approximation-Based Data Structure for Similarity Search", The European Esprit Project Hermes (Project No. 9141), 1997, pp. 1-25, Morgan Kaufmann.

Pravin M. Vaidya, "An O (N Log N) Algorithm for the All-Nearest-Neigbors Problem", Discrete & Computational Geometry 4, 1989, pp. 101-115, vol. 4, Issue 2.

Kevin Beyer, Jonathan Goldstein, Raghu Ramakrishnan and Uri Shaft, "When is "Nearest Neighbor" Meaningful?", Proceedings of the 7th ICDT, 1998, pp. 217-235, Springer-Verlag Berlin, Heidelberg, Germany.

Sunil Arya, David M. Mount, Nathan S. Netanyahu, Ruth Silverman and Angela Y. Wu, "An Optimal Algorithm for Approximate Nearest Neighbor Searching in Fixed Dimensions", 1998, pp. 891-923, vol. 45, No. 6, Journal of the ACM, New York, NY, USA.

Pavel Zezula, Guiseppe Amato, Vlastislav Dohnal and Michal Batko, "Similarity Search the Metric Space Approach", Book, 2006, pp. 220, vol. 32, Birkhaeuser, Basel, Switzerland.

Chung-Min Chen and Yibei Ling, "A Sampling-Based Estimator for Top-K Selection Query", 18th International Conference on Data Engineering, 2002, pp. 617-627, Telcordia Technologies, Morristown, NJ, USA.

Hanan Samet, "Foundations of Multidimensional and Metric Data Structures", Book, 2006, pp. 993, Morgan Kaufmann.

* cited by examiner

IMAGING METHOD AND APPARATUS WITH OPTIMIZED GRAYSCALE VALUE WINDOW DETERMINATION

CROSS-REFERENCE TO RELATED APPLICATION

This application claims the priority, under 35 U.S.C. §119, of German patent application DE 10 2011 003 138.3, filed Jan. 25, 2011; the prior application is herewith incorporated by reference in its entirety.

BACKGROUND OF THE INVENTION

Field of the Invention

The present invention relates to a tomographic imaging method, more particularly a mammography method, in which an optimized grayscale value window is determined, and also to an apparatus and a related computer program product.

In a tomosynthesis method, a three-dimensional image is generated from a plurality of two-dimensional projections. An X-ray apparatus with an X-ray beam source and a detector is used to generate a first two-dimensional image or a first projection of the tissue to be examined, through which tissue the X-ray beam passes. Here, the two-dimensional image represents the attenuation of the X-ray radiation by the tissue in the volume or in the breast. A second two-dimensional image or a second projection of the same tissue or volume is recorded after the beam source and/or the detector was moved into a second position. After a plurality of two-dimensional images were recorded, a three-dimensional tomosynthesis image can be generated by means of a reconstruction.

Mammography is a field of application of the three-dimensional imaging method mentioned above. An image generation device typically used in mammography includes a pivotable X-ray beam source and a stationary X-ray detector. The tissue to be examined is positioned over the stationary detector, with the tissue to be examined being compressed and not being in a natural shape. The X-ray source is subsequently pivoted over a number of steps or continuously, for example within a range of +/−25°, and the stationary detector is used to record a plurality of two-dimensional X-ray images from different pivot positions of the X-ray beam source. It goes without saying that it is also possible to use a plurality of stationary X-ray beam sources or to merely displace the X-ray beam source in a translational fashion. It is also possible for the detector to be displaced or pivoted counter to the movement of the X-ray source. In the case of craniocaudal recordings, the X-ray beam source(s) emit(s) X-ray beams from positions that are arranged along a line running parallel to the axis running from shoulder to shoulder of a patient. A beam path parallel to the chest wall can result in the entire tissue of the breast being imaged and the thorax not being irradiated. A three-dimensional image is generated from the plurality of two-dimensional X-ray images by means of the reconstruction.

Pertinent prior art imaging methods and devices for mammography are described, for example, in the following commonly assigned patents and published patent applications: U.S. Pat. No. 7,945,014 B2 and DE 10 2006 046 741 A1; US 2010/0034450 A1 and DE 10 2008 004 473 A1; US 2011/0122992 A1 and DE 10 2008 033 150 A1; U.S. Pat. No. 7,965,812 B2 and EP 2 138 098 A1; and US 2009/0310844 A1 and DE 10 2008 028 387 A1.

In the prior art, so-called filtered back projections are used to reconstruct a three-dimensional image from a plurality of two-dimensional images; by way of example, these filtered back projections are described in chapter 10.5 of Imaging Systems for Medical Diagnostics, Arnulf Oppelt, Publicis Corporate Publishing, Erlangen, ISBN 3-89578-226-2. These filtered back projection reconstruction methods display reconstructed images with a comparatively high contrast and comparatively great detail, but lose information in respect of the relative tissue density in the case of tomosynthesis with a restricted scanning angle as a result of the missing data. This is the result of certain filter kernels removing low-frequency components. In general, digital breast tomosynthesis (DBT) is afflicted by incomplete data and poor quantum statistics, which is restricted by the overall dose absorbed in the breast. The breast mainly consists of glandular tissue, fatty tissue, connective tissue and blood vessels. The X-ray attenuation coefficients of these types of tissue are very similar, making the evaluation of three-dimensional mammography images significantly harder. The main field of application of imaging methods in mammography is the early detection of cancerous tissue. This is made more difficult by the fact that cancerous tissue has a similar X-ray attenuation coefficient to other types of tissue.

By way of example, mammography methods are described in chapter 12.6 of Imaging Systems for Medical Diagnostics, Arnulf Oppelt, Publicis Corporate Publishing, Erlangen, ISBN 3-89578-226-2.

Tissue regions with different densities, which cause different attenuation of the X-ray beam, are illustrated using different grayscale values in a tomography recording or a slice image. The density information from CT recordings is measured in so-called Hounsfield units (HU). Water corresponds to 0 HU and air corresponds to −1000 HU. However, the eye is not capable of resolving several thousand grayscale value steps. Hence, depending on the tissue to be diagnosed, merely part of the entire grayscale range can be displayed for the human eye. This process is referred to as windowing.

The values for the windowing are usually defined by the width and the center point of the grayscale range, or by the maximum value and minimum value of the grayscale value window. A soft tissue window can be referred to as 350/50, which means that the grayscale range from −125 HU to 225 HU is displayed. A bone window can be specified by 2000/500. The soft tissue window is suitable for displaying soft tissue, whereas a bone window is suitable for displaying bones. Grayscale values situated outside of the specified window are not displayed on a display apparatus or in a printout. In general terms, windowing is described in Medizinische Informatik und Bioinformatik [Medical computer science and biological computer science], Martin Dugas, Karin Schmidt, Springer, ISBN 3-540-42568-3.

The predefined prescription of grayscale value windows is not possible in tomosynthesis because recordings were only created over a limited angular range, particularly in breast tomosynthesis.

Currently known methods for determining windowing comprise the segmentation of the relevant region of a recording (ROI) or of the organ to be examined, the calculation of a histogram of a segmented ROI (region of interest), optional smoothing of the histogram and the use of an ad-hoc algorithm, which was developed specifically for the respective modality and for the respective reconstruction algorithm. The ad-hoc algorithm must be newly developed or newly optimized for each modality and for each reconstruction algorithm. This can lead to a different brightness distribution in the reconstructed volume, depending on the utilized modality. Such an approach requires a time-consuming optimization of the algorithm for automatically determining the windowing. A further problem lies in the fact that different radiologists prefer different visual impressions. While some radiologists prefer brighter views, other radiologists prefer darker images. It is self-evident that some radiologists prefer more contrast-rich representations, while other radiologists prefer softer representations. Thus, the representation considered optimum by one radiologist may be considered non-optimum by another radiologist. It follows that the developers have to optimize the parameters of the automated windowing algorithm manually for each radiologist and individually examine the resulting image quality therefore in hundreds of test images. This procedure requires a plurality of iteration cycles with an assessment of the quality of the images and the subsequent improvement of the algorithms.

SUMMARY OF THE INVENTION

It is accordingly an object of the invention to provide an imaging method with optimized grayscale window determination which overcome the above-mentioned disadvantages of the heretofore-known devices and methods of this general type and which provides for an improved algorithm for determining the grayscale value window.

With the foregoing and other objects in view there is provided, in accordance with the invention, an imaging method, which comprises the following steps:
  displaying a plurality of training data sets on a display apparatus;
  selecting a grayscale value setting for each training data set that should be displayed on the display apparatus with the grayscale value setting;
  computing a feature set with at least one feature to each training data set;
  storing the grayscale value setting selected for the training data set and the feature set assigned to the training data set, for each of the plurality of training data sets;
  computing a feature set with at least one feature to an examination data set;
  automatically selecting the grayscale value setting for the examination data set depending on the feature set of the examination data set and depending on the feature set of the training data sets; and
  displaying the examination data set with the automatically selected grayscale value setting on the display apparatus.

In other words, the objects of the invention are achieved by the imaging method according to the invention. A plurality of training data sets are displayed on a display apparatus. A grayscale value setting is selected for each training data set that should be used to display the training data set on the display apparatus. A feature set with at least one feature is assigned to each training data set. The grayscale value setting selected for the training data set and the feature set assigned to the training data set are stored for each of the plurality of training data sets.

Training data sets can be tomography recordings used to find an optimum grayscale value window for the respective modality, the respective algorithm and the respective user and/or a plurality of users. An examination data set is a recording for examining a patient, for example a new patient for whom no training data set has been created yet. The examination data sets can be created within the scope of screening a plurality of patients. The training data sets and examination data sets may in each case be tomography recordings, for example an X-ray recording, and/or reconstructed tomosynthesis slice images. The training data sets and examination data sets may also be an image that was generated using any modality. However, the training data sets and examination data sets can also be a data set that was generated from a plurality of recordings, which were created using any modality. The training data sets and the examination data set can represent a volume. The volume can be generated by means of a tomosynthesis method. Furthermore, the training data sets and the examination data sets can be generated by means of multi-modal techniques.

A feature set with at least one feature is assigned to an examination data set. An examination data set is a tomography recording which was recorded using a specific modality and/or algorithm and should be examined by a particular radiologist or a plurality of radiologists in order to make a diagnosis. The grayscale value setting for displaying the examination data set is selected automatically depending on the feature set of the examination data set and depending on the feature set of the training data sets. The examination data set is displayed with the automatically selected grayscale value setting on the display apparatus.

The method can be carried out separately for each radiologist. The method can also be carried out separately for each modality, for example tomosynthesis, 2D mammography, MRI or CT. The method can be carried out separately for each utilized imaging algorithm. This allows each radiologist to select his preferred grayscale value settings for each modality and each imaging algorithm. To this end, use is made of the so-called training data sets, in which the radiologist sets his preferred grayscale value settings for each modality and the method automatically stores the grayscale value setting selected by the radiologist. Furthermore, features of the learning tomography algorithm are calculated and stored.

If the radiologist wishes to make a diagnosis by means of the imaging device, the examination data set recorded by the modality is automatically displayed using the grayscale value setting preferred by the radiologist. The method automatically selects the grayscale value setting preferred by the radiologist depending on the feature set of the examination data set and the respective feature set of the plurality of training data sets.

The training data sets can display the same tissue region of different patients, which training data sets are generated using the same modality and the same imaging algorithm. By way of example, the tissue region can be the mamma, the modality can be a DBT apparatus and the imaging algorithm can be a back projection. It follows that the method establishes, separately for each radiologist or for a group of radiologists, the optimum grayscale value setting for different breast thicknesses, breast densities, breast compositions, radiation doses and/or other parameters.

At least one feature of the feature set can be extracted from the training data sets. Furthermore, at least one feature of the feature set can be extracted from the examination data set.

It is possible to determine the tissue density, the component of fatty tissue, the component of glandular tissue, the component of scarred tissue, the component of bright tissue and/or the component of calcified tissue from the training data sets and the examination data set as feature or features of the feature set. It is possible to extract any further features from the training data set and the examination data set and assign these thereto.

It is possible to assign the radiation dose, for example from an X-ray recording, to each of the training data sets and the examination data set as one feature of the feature set. It is possible to assign more external features, which are not extracted from one of the tomography recordings, to the corresponding training data set and the examination data set. By way of example, these external features can comprise the tissue type, the size of the tissue region, the size of the breast, the age of the patient, the sex of the patient, the height of the patient, the weight of the patient, etc.

It is possible to determine the training data set the feature set of which has the greatest correspondence to the examination data set. The examination data set with that grayscale value setting is displayed, which is assigned to the training data set whose feature set has the greatest correspondence to the feature set of the examination data set. An examination data set, which is generated with a modality for examining a patient, is displayed with the grayscale value setting that the radiologist set for a training data set of a similar type. This ensures that the examination data set is displayed with the grayscale value setting that best corresponds to the preferences of the radiologist. This method can be a simple nearest-neighbor method. This method can be applied when there is a large number of training data sets, which have a great variety and the features of which are evenly distributed over the feature space.

It is possible to interpolate between the grayscale value settings of a plurality of training data sets depending on the determined correspondence of the feature set of the examination data set with the feature sets of the plurality of training data sets. The features in the feature sets can be provided with different weightings. This procedure allows an optimized grayscale value setting to be determined from the grayscale value settings of a plurality of training data sets.

It is possible to generate a transformation between a feature set and the grayscale value settings by interpolating between the grayscale value settings for a plurality of training data sets. The transformation can generate the optimum grayscale value settings from the feature set of an examination data set. The transformation can be displayed mathematically as follows:

$$y_1 = a_{11}x_1 + a_{12}x_2 + \ldots + a_{1n}x_n + b_1;$$

$$y_2 = a_{21}x_1 + a_{22}x_2 + \ldots + a_{2n}x_n + b_2;$$

where $x_1$ to $x_n$ are features of a feature set, $y_1$ and $y_2$ are grayscale value settings and $a_{11}$ to $a_{2n}$ are coefficients of the transformation.

The transformation can have a matrix with more than two rows. The grayscale value settings can be a mean value and a width of the grayscale value window. However, the grayscale value settings can also be any other values of the grayscale value window.

The transformation between a feature set and the grayscale value settings can be established by using a regression analysis, using a linear regression model, using a simple linear regression, using a logistic regression, using a nonlinear regression, using a piecewise regression and using a nearest-neighbor model.

The correspondence of the feature set of the examination data set to the feature sets of the plurality of training data sets can be determined by means of a regression analysis, a linear regression model, a simple linear regression, a logistic regression, a nonlinear regression, a piecewise regression, a nearest-neighbor model, etc. A plurality of different models, which correspond to the most common preferences of radiologists, may be predefined. By way of example, the most commonly used model, the model with the highest contrast, the model with the lowest noise and the softest model, the calcification model, the tissue model (mass model), etc. may be defined or calculated in advance. An adaptive learning algorithm can be provided for radiologists who do not approve of the predefined models.

The radiologist is able to modify the grayscale value setting of the displayed examination data set. The modified grayscale value setting and the feature set of the examination data set are stored as grayscale value setting and as feature set of a training data set. This increases the number of training data sets. Furthermore, the representation is adaptively improved because the preferences of the respective radiologist are established in the case of the respective modality and the imaging algorithm, and the number of available training data sets for the respective radiologist, the respective modality and the imaging algorithm is increased.

The grayscale value setting can include the grayscale value range of the examination data set, which should be displayed on a display apparatus, the contrast of the displayed image, the mean brightness of the displayed image and/or parameters of a false-color representation of the displayed image. The term "grayscale value" does not restrict the invention to a representation without colors. The invention is also applicable in the case of a color representation.

The above-described method can be carried out separately for each radiologist and/or for each different modality. Hence an optimized grayscale value setting for each modality is generated for each individual radiologist. It is thus guaranteed that each radiologist obtains the tomography recordings in the desired representation.

With the above and other objects in view there is also provided a representation learning apparatus which is configured to carry out the above-described method.

The invention also discloses an imaging system with the representation learning apparatus.

Furthermore, the invention relates to a computer program product which can be loaded into a memory of a computer, or is loaded therein. When the program code is executed on the computer, it carries out the above-described method.

Other features which are considered as characteristic for the invention are set forth in the appended claims.

Although the invention is illustrated and described herein as embodied in imaging method with optimized grayscale value window determination, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

The invention will be explained below with reference to mammography. It is understood that the invention is also applicable to other fields.

Figure 1:
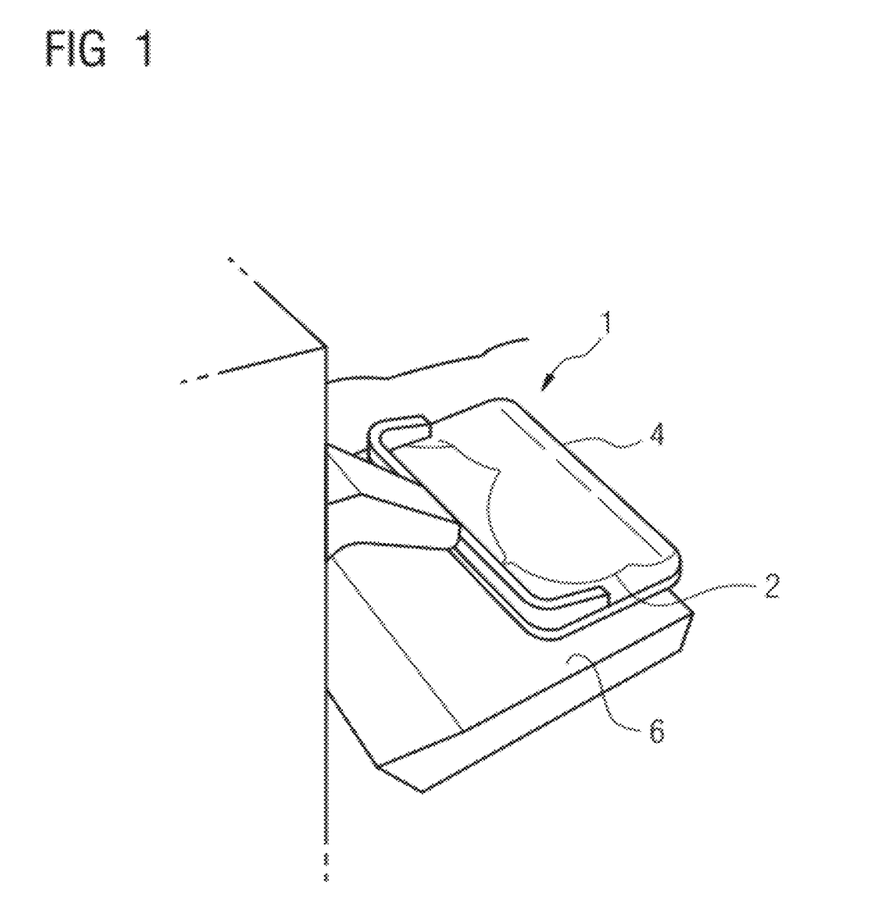
FIG. 1 shows an imaging system for a mammography process, in which the breast is compressed in order to carry out recordings of the interior of the breast.

Referring now to the figures of the drawing in detail and first, particularly, to FIG. 1 thereof, there is shown a first imaging modality, which has a compression plate 4 and a compression table 6, between which the breast 2 is clamped. The breast is usually compressed in this fashion until a predetermined compression force is reached. A plurality of X-ray sources or at least one movable X-ray source (not illustrated) can be arranged over the compression plate 4. An X-ray detector can be arranged in or below the table 6. This device can be used to capture projections from different directions by means of X-ray radiation, from which, as described at the outset, it is possible to generate slice images.

The compressed breast is captured in the mediolateral oblique (MLO) position in the first imaging modality 1.

Figure 2:
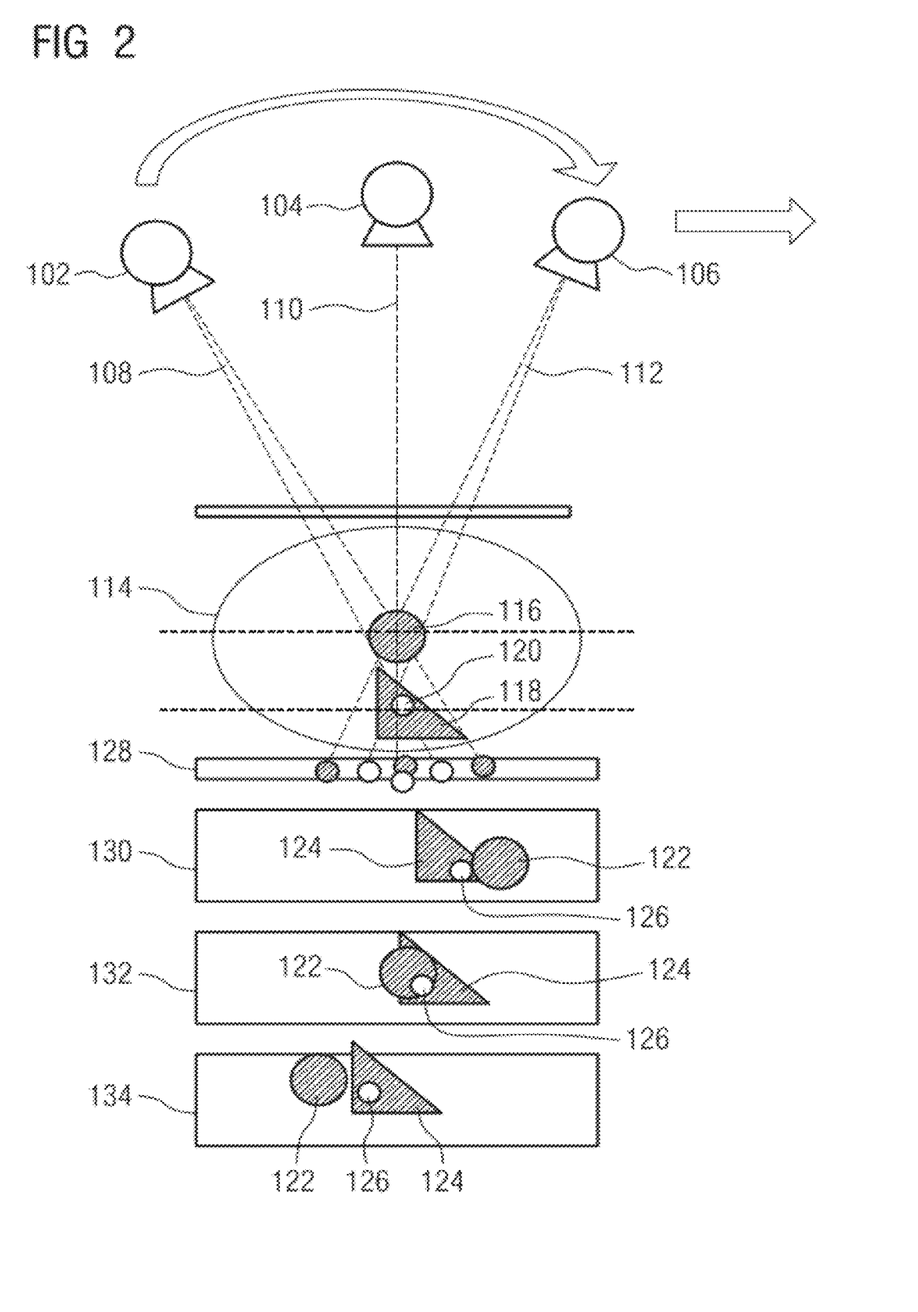
FIG. 2 schematically shows the generation of projection recordings.

The method for generating the projections is explained with reference to FIG. 2. A plurality of X-ray sources 102, 104, 106 are arranged over an angular range of approximately 50°. It is possible for 25 X-ray sources to be arranged, and so 25 projections can be generated. As an alternative to this, it is possible for an X-ray source to be pivoted over an angular range of 50° such that 25 projection recordings are generated. The first X-ray source 102 emits a first X-ray beam 108, which passes through the breast 114 and is attenuated by a first tissue region 116, a second tissue region 118 and a third tissue region 120. An X-ray detector 128 generates a first projection recording 130, in which the first tissue region image 122, the second tissue region image 124 and the third tissue region image 126 are in a first arrangement. The second X-ray beam source 104 emits a second X-ray beam 110, at a different angle, to the breast 114, the first tissue region 116, the second tissue region 118 and the third tissue region 120. These tissue regions are recorded by the second projection recording 132 and are in an arrangement that differs from that of the first projection recording 130. The third X-ray source 106 emits a third X-ray beam 112 to the breast at a further angle and this beam generates a third arrangement of the first tissue region image 122, second tissue region image 124 and third tissue region image 126 in the third projection recording 134.

Figure 3:
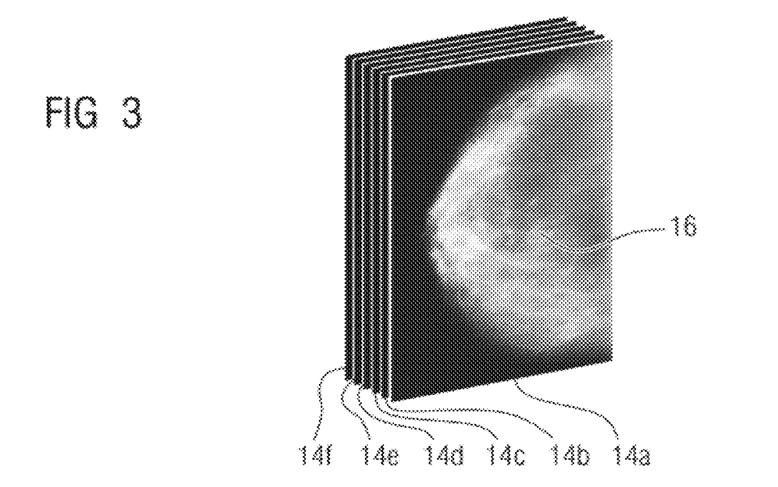
FIG. 3 shows slice images produced by way of DBT.

FIG. 3 shows a plurality of slice images, which were captured by way of the imaging modality, i.e. by means of DBT (digital breast tomosynthesis). They form the first image volume of the breast 16. A plurality of slice images 14a to 14f are shown. Since cancerous breast tissue has a similar attenuation coefficient as healthy tissue, it is difficult to assess whether cancerous tissue is present. This results in false positive or false negative diagnoses.

The functionality of the DBT-type modality was described at the outset and is known to a person skilled in the art from, for example, Imaging Systems for Medical Diagnostics, Arnulf Oppelt, Publicis Corporate Publishing, Erlangen, ISBN 3-89578-226-2; hence it is not described in any more detail, but the publication is incorporated herein by reference.

Figure 4:
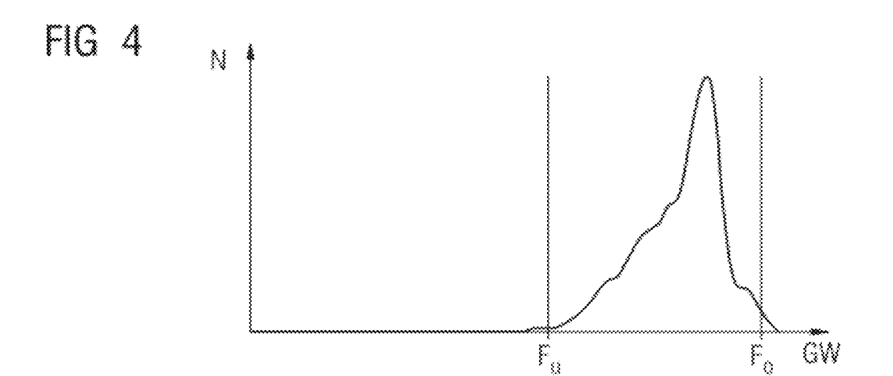
FIG. 4 shows the selection of a grayscale value window in a histogram.

FIG. 4 shows a histogram of a tomosynthesis recording, as generated by an imaging modality. The grayscale value is plotted on the abscissa and the number of pixels that have the corresponding value is plotted on the ordinate.

Figure 5:
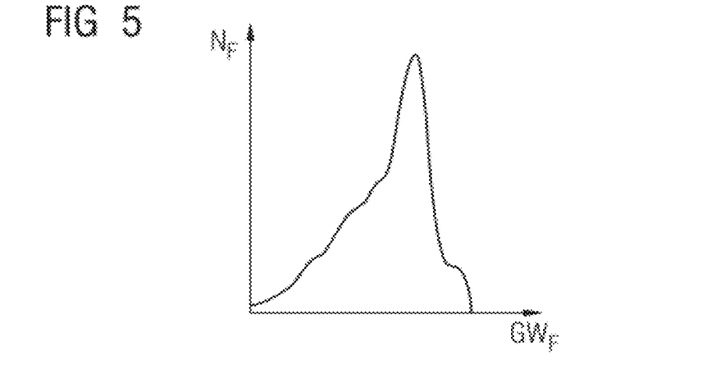
FIG. 5 shows a histogram with a grayscale value window.

The breast of the patient should be examined in the example illustrated in FIGS. 4 and 5. It follows that a lower limit $W_L$ of the window is defined as lowest intensity value to be displayed and an upper limit $W_U$ of the window is defined as greatest grayscale value to be displayed. This grayscale value range is displayed on a display device, for example a monitor, as a result of which the histogram as per FIG. 5 emerges for the display on the monitor.

Since the human eye cannot resolve the large grayscale value range as per FIG. 4 sufficiently finely, only the window defined by the limits $W_L$ and $W_U$ is used for the representation on a display apparatus or on a printout, as shown in FIG. 5. This allows the human observer to identify relatively small brightness differences, as may be necessary for a diagnosis, for example of breast cancer.

Figure 6:
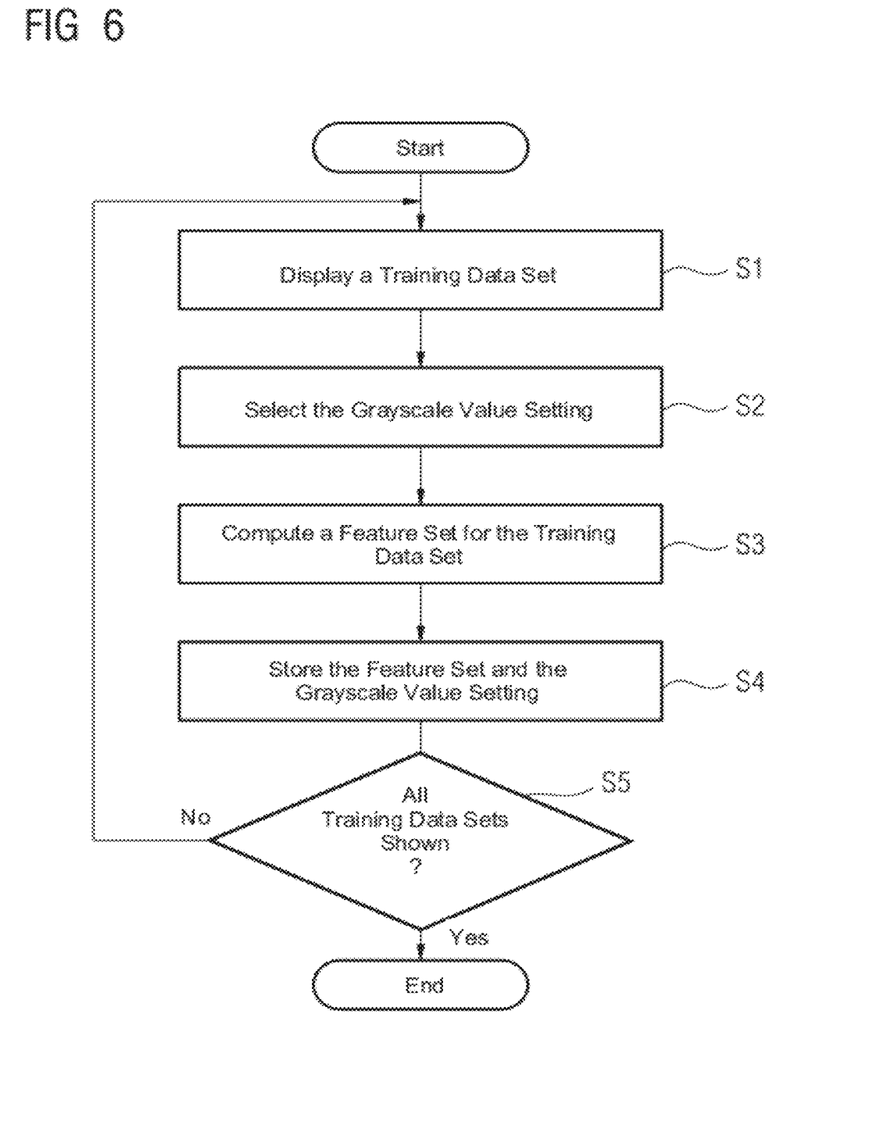
FIG. 6 shows a flowchart of a process sequence for automatically establishing a suitable grayscale value window.

FIG. 6 shows a flowchart for determining the optimum grayscale value setting. In step S1, a training data set is displayed on a display apparatus, for example a monitor. The training data set can be a mammography slice image, which was reconstructed from a plurality of X-ray recordings. In step S2, a radiologist selects the optimum grayscale value setting for the training data set. The optimum grayscale value setting may comprise the limits of the grayscale value window, the mean brightness, the contrast, the gamma correction, etc. In step S3, a feature set is assigned to the training data set. The feature set can have features extracted from the training data set, for example the tissue density, the component of fatty tissue, the component of glandular tissue, the component of scarred tissue, the component of bright tissue, the component of calcified tissue, etc. External features can also be assigned to the training data set, for example the radiation dose used in the modality for generating the training data set, the height of the patient, the size of the tissue region, the type of tissue region, the age of the patient, etc.

The feature set and the grayscale value setting are stored in step S4. A check is carried out in step S5 as to whether all training data sets have been displayed and the corresponding grayscale value settings have been selected. The training data sets can represent the same tissue region of different patients. By way of example, the training data sets can represent the breasts of different patients. The method according to the invention is carried out separately for each radiologist. That is to say, an assignment of feature sets and grayscale value settings is established separately for each radiologist. Moreover, this assignment is generated for each modality and each imaging algorithm. In other words, it is possible to determine an assignment of feature sets and grayscale value settings per modality for each radiologist.

Figure 7:
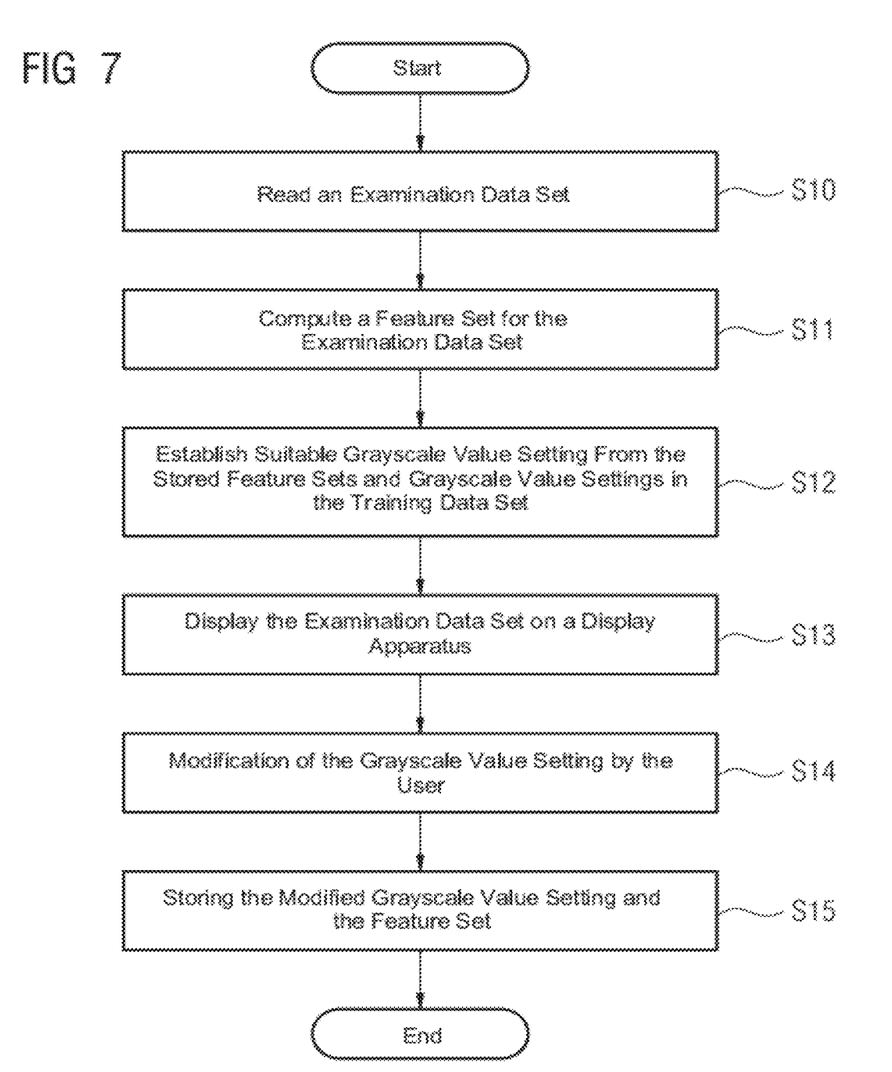
FIG. 7 shows a flowchart of a process sequence for displaying an examination data set with a suitable grayscale value representation.

FIG. 7 shows a flowchart for determining the suitable grayscale value setting for an examination data set. The examination data set is recorded in order to examine a patient. By way of example, the examination data set can be recorded using a DTM modality (DTM, digital tomosynthesis mammography). In step S10, the examination data set is read from the modality or a memory. In step S11, a feature set is assigned to the examination data set. This feature set can have the features and external features extracted from the examination data set, which features and external features were described above in step S3 with reference to the training data set.

The suitable grayscale value setting is established in step S12 from the stored feature sets and grayscale value settings of the training data sets. To this end, use can be made of the above-described transformation, a linear regression model, a simple linear regression, a logistic regression, a nonlinear regression, a robust regression, a piecewise regression and/or a nearest-neighbor algorithm. It is possible to weight individual features of the feature set more strongly than other features.

The examination data set with the grayscale value setting established in step S12 is displayed on a display apparatus in step S13.

The radiologist can modify the grayscale value setting in an optional step S14. The modified grayscale value setting and the feature set of the examination data set can be stored as additional learning data in the optional step S15. That is to say the examination data set is treated like a training data set after modification of the grayscale value setting. The data with feature sets and grayscale value setting can be permanently updated in accordance with the preferences of the radiologist for the respective modality. Thus the examination data sets are also used as training data sets after modification of the grayscale value setting.

According to the invention, it was proposed to capture preferences of experts only once for a plurality of training data sets (development set) of a specific modality, which is respectively obtained with a specific reconstruction algorithm. The plurality of training data sets must contain a sufficient number of recordings for capturing the variations in the appearance of the images. By way of example, in digital mammography or digital breast tomosynthesis, the majority of training data sets should have a different breast density, a different amount of fatty tissue and glandular tissue, a different radiation dose, a different breast thickness, a different amount of calcification and other bright structures in the breast, etc.

The radiologist must set the grayscale value setting according to his preferences in the plurality of training data sets. The width of the window, the mean value of the window and/or other parameters of the window, for example the minimum intensity and the maximum intensity, the brightness and the contrast are stored for each training data set and are then used as input data for determining the suitable grayscale value setting for the examination data set of the automatic window algorithm according to the invention.

Use is then made of a feature set for characterizing the breast density, the amount of fatty tissue and glandular tissue, the radiation dose, the breast thickness, the amount of calcification and other bright structures, e.g. scars, for each training data set. The set of these features can be calculated using segmentation algorithms and breast density determination algorithms, computer-assisted diagnosis algorithms for establishing the amount of calcifications, masses and the scars in the breast.

Furthermore, the (compressed) breast thickness, the compression force, the radiation dose, the age of the patient, and the presence of an implant can be stored in the DICOM (Digital Imaging and Communications in Medicine) header or obtained from the HIS system (Hospital Information System) or from the RIS system (Radiology Information System). As an alternative or in addition thereto, use can be made of a histogram or a smoothed histogram. A regression analysis as a statistical method is used to assign the feature set to the resulting window settings or grayscale value settings or to estimate the connections between the feature set of a tomography recording and the grayscale value setting. Then the same feature set can be calculated for each examination data set that was generated by the same modality and obtained by the same reconstruction algorithm, and the grayscale value setting is obtained using the regression model calculated in advance. As an alternative to this, use can be made of a nearest-neighbor algorithm in order to use the grayscale value setting for the most similar training data set in the plurality of training data sets. A plurality of regression models or nearest-neighbor models can be created for each modality and each reconstruction algorithm, which use the grayscale value settings of different radiologists with different preferences in respect of the image representation. Furthermore, adaptive learning can be implemented if the automatic window algorithm according to the invention is supplied with new data and the plurality of training data sets is augmented by examination data sets in which the radiologist modifies the grayscale value setting.

Individual preferences of a radiologist are taken into account in the regression model or the nearest-neighbor model. If a specific radiologist uses the system, his preferred model, i.e. the assignment of a feature set to a grayscale value setting preferred by him, is loaded. The examination data sets are windowed according to the preferences of the radiologist.

The invention discloses a method for automatically learning and setting the window parameters or grayscale value settings of different modalities, different reconstruction algorithms and different preferences of individual users with the aid of a machine learning algorithm. The algorithm is capable of adaptive learning.

Figure 8:
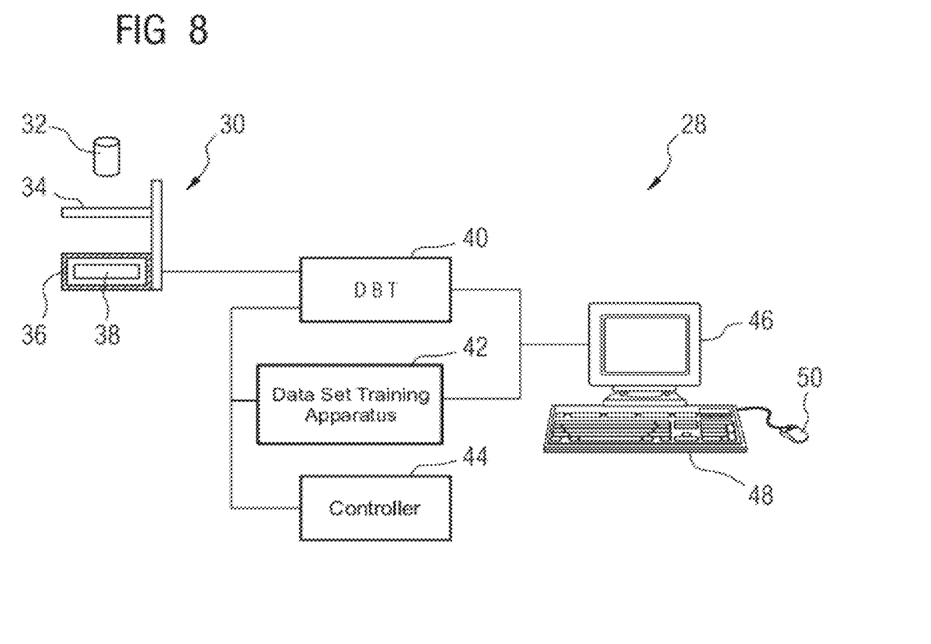
FIG. 8 shows an imaging system according to the invention.

FIG. 8 shows a medical system 28 in an operation environment. The medical system 28 comprises an imaging modality 30 with an X-ray beam source 32, a compression plate 34, a compression table 36 and an X-ray detector 38. The X-ray source 32 can be arranged in a pivotable fashion in order to generate projection recordings from different angles, which are captured by means of the X-ray detector 38.

The projections recorded by the X-ray detector 38 are transmitted to a DBT apparatus 40, where slice recordings are generated that are displayed on the display apparatus 46. A control apparatus 44 can, independently or in conjunction with the DBT apparatus 40, establish changed tissue, which is also displayed on the display apparatus 46. The changed tissue can have cancerous tissue, a carcinoma, a lump or any other medically relevant diagnosis. A radiologist can display the changed tissue by means of the input apparatus 48, 50 such that the diagnosis can be made as precisely as possible. As a reaction to user inputs, a representation learning apparatus 42 can carry out the above-described method for assigning a grayscale value setting to training data sets and the above-described method for establishing a suitable grayscale value setting for displaying the examination data set on the basis of the features of the examination data set. The control apparatus 44 controls the operation of both the DBT apparatus 40 and that of the representation learning apparatus 42.

Finally, reference is made to the fact that the description of the invention and the exemplary embodiments should not, as a matter of principle, be understood as being restrictive in view of a particular physical implementation of the invention. More particularly, a person skilled in the art considers it obvious that the invention can be wholly or partly implemented as software and/or hardware, and/or can be implemented distributed over a plurality of physical products—more particularly also computer program products in this case.

The following list of reference numerals used in the above specification may aid the reader in reading the description:
2 Breast
4 Compression plate
6 Table
14 Slice images
28 Medical system
30 Modality
32 X-ray beam source
34 Compression plate
36 Compression table
38 X-ray detector
40 DBT apparatus 42 Representation learning apparatus
44 Control apparatus
46 Display apparatus
50 Input apparatus
102 First X-ray source
104 Second X-ray source
106 Third X-ray source
108 First X-ray beam
110 Second X-ray beam
112 Third X-ray beam
114 Breast
116 First tissue region
118 Second tissue region
120 Third tissue region
122 First tissue region image
124 Second tissue region image
126 Third tissue region image
128 Detector element
130 First projection recording
132 Second projection recording
134 Third projection recording

The invention claimed is:

1. A tomographic imaging method, which comprises the following steps:
displaying a plurality of training data sets on a display apparatus;
selecting a grayscale value setting for each training data set that should be displayed on the display apparatus with the grayscale value setting;
assigning a feature set with at least one feature to each training data set;
storing the grayscale value setting selected for the training data set and the feature set assigned to the training data set, for each of the plurality of training data sets;
assigning a feature set with at least one feature to an examination data set;
automatically selecting the grayscale value setting for the examination data set depending on the feature set of the examination data set and depending on the feature set of the training data sets;
displaying the examination data set with the automatically selected grayscale value setting on the display apparatus; and
generating a transformation between a feature set of the examination data set and the grayscale value settings for the examination data set by interpolating between the grayscale value settings for a plurality of training data sets;
wherein the transformation between the feature set of the examination data set and the grayscale value settings for the examination data set is determined by at least one of the following steps:
using a regression analysis;
using a linear regression model;
using a simple linear regression;
using a logistic regression;
using a nonlinear regression;
using a piecewise regression; and
using a nearest-neighbor model.

2. The imaging method according to claim 1, wherein the training data sets display the same tissue regions, created with the same modality, of a plurality of different patients.

3. The imaging method according to claim 1, which comprises:
extracting at least one feature of the feature set from the training data sets; and
extracting at least one feature of the feature set from the examination data set.

4. The imaging method according to claim 1, which further comprises carrying out one or more of the following steps:
determining a tissue density from the training data sets and the examination data set as one feature of the feature set;
determining a component of fatty tissue from the training data sets and the examination data set as one feature of the feature set;
determining a component of glandular tissue from the training data sets and the examination data set as one feature of the feature set;
determining a component of scarred tissue from the training data sets and the examination data set as one feature of the feature set;
determining a component of bright tissue from the training data sets and the examination data set as one feature of the feature set; and
determining a component of calcified tissue from the training data sets and the examination data set as one feature of the feature set.

5. The imaging method according to claim 1, which further comprises assigning a radiation dose to each of the training data sets and the examination data set as a feature of the feature set.

6. The imaging method according to claim 1, which further comprises the following steps:
determining the training data set whose feature set has a greatest correspondence to the examination data set; and
displaying the examination data set with a grayscale value setting that is assigned to the training data set whose feature set has the greatest correspondence to the examination data set.

7. The imaging method according to claim 1, which further comprises the following steps:
modifying the grayscale value setting of the displayed examination data set to define a modified grayscale value setting; and
storing the modified grayscale value setting and the feature set of the examination data set as the grayscale value setting and the feature set of a training data set.

8. The imaging method according to claim 1, wherein the grayscale value setting comprises at least one of the following:
a grayscale value range of the examination data set to be displayed on a display apparatus;
a contrast of the displayed image;
a mean brightness of the displayed image; and
parameters of a false-color representation of the displayed image.

9. A representation learning apparatus, configured to carry out the following method steps:
displaying a plurality of training data sets on a display apparatus;
selecting a grayscale value setting for each training data set that should be displayed on the display apparatus with the grayscale value setting;
assigning a feature set with at least one feature to each training data set;
storing the grayscale value setting selected for the training data set and the feature set assigned to the training data set, for each of the plurality of training data sets;
assigning a feature set with at least one feature to an examination data set;

automatically selecting the grayscale value setting for the examination data set depending on the feature set of the examination data set and depending on the feature set of the training data sets;

displaying the examination data set with the automatically selected grayscale value setting on the display apparatus; and generating a transformation between a feature set of the examination data set and the grayscale value settings for the examination data set by interpolating between the grayscale value settings for a plurality of training data sets;

wherein the transformation between the feature set of the examination data set and the grayscale value settings for the examination data set is determined by at least one of the following steps:
using a regression analysis;
using a linear regression model;
using a simple linear regression;
using a logistic regression;
using a nonlinear regression;
using a piecewise regression; and
using a nearest-neighbor model.

10. An imaging system, comprising a representation learning apparatus for carrying out the following method steps:
displaying a plurality of training data sets on a display apparatus;
selecting a grayscale value setting for each training data set that should be displayed on the display apparatus with the grayscale value setting;
assigning a feature set with at least one feature to each training data set;
storing the grayscale value setting selected for the training data set and the feature set assigned to the training data set, for each of the plurality of training data sets;
assigning a feature set with at least one feature to an examination data set;
automatically selecting the grayscale value setting for the examination data set depending on the feature set of the examination data set and depending on the feature set of the training data sets;
displaying the examination data set with the automatically selected grayscale value setting on the display apparatus; and
generating a transformation between a feature set of the examination data set and the grayscale value settings for the examination data set by interpolating between the grayscale value settings for a plurality of training data sets;
wherein the transformation between the feature set of the examination data set and the grayscale value settings for the examination data set is determined by at least one of the following steps:
using a regression analysis;
using a linear regression model;
using a simple linear regression;
using a logistic regression;
using a nonlinear regression;
using a piecewise regression; and
using a nearest-neighbor model.

11. A non-transitory computer program product, comprising computer-executable code in non-transitory form to be loaded into, or loaded in, a memory of a computer, and configured to carry out the following executed steps on the computer:
displaying a plurality of training data sets on a display apparatus;
selecting a grayscale value setting for each training data set that should be displayed on the display apparatus with the grayscale value setting;
assigning a feature set with at least one feature to each training data set;
storing the grayscale value setting selected for the training data set and the feature set assigned to the training data set, for each of the plurality of training data sets;
assigning a feature set with at least one feature to an examination data set;
automatically selecting the grayscale value setting for the examination data set depending on the feature set of the examination data set and depending on the feature set of the training data sets;
displaying the examination data set with the automatically selected grayscale value setting on the display apparatus; and
generating a transformation between a feature set of the examination data set and the grayscale value settings for the examination data set by interpolating between the grayscale value settings for a plurality of training data sets;
wherein the transformation between the feature set of the examination data set and the grayscale value settings for the examination data set is determined by at least one of the following steps:
using a regression analysis;
using a linear regression model;
using a simple linear regression;
using a logistic regression;
using a nonlinear regression;
using a piecewise regression; and
using a nearest-neighbor model.

* * * * *